United States Patent [19]

Florek

[11] Patent Number: 4,480,637
[45] Date of Patent: Nov. 6, 1984

[54] ORTHOPAEDIC APPLIANCE FOR USE IN TREATING FRACTURED CLAVICLES

[76] Inventor: Florian F. Florek, 104 High St., Edinboro, Pa. 16412

[21] Appl. No.: 482,405

[22] Filed: Apr. 6, 1983

[51] Int. Cl.³ .............................................. A61F 5/40
[52] U.S. Cl. .............................. 128/94; 128/DIG. 19
[58] Field of Search ............... 128/94, 87 R, DIG. 19, 128/83, 155, 156; 604/362

[56] References Cited

U.S. PATENT DOCUMENTS

| | | | |
|---|---|---|---|
| 3,404,680 | 10/1968 | Gutman et al. | 128/94 |
| 3,508,551 | 4/1970 | Walters et al. | 604/362 |
| 3,965,907 | 6/1976 | Hardy et al. | 604/362 |
| 4,198,964 | 4/1980 | Honneffer | 128/94 X |
| 4,220,149 | 9/1980 | Mims, Jr. | 128/94 |
| 4,244,369 | 1/1981 | McAvinn et al. | 604/362 |

*Primary Examiner*—John D. Yasko
*Attorney, Agent, or Firm*—Howson and Howson

[57] ABSTRACT

An orthopaedic appliance for use in treating a patient having a clavicle fractured between its proximal and distal ends. The appliance comprises a belt adapted to surround the abdomen of the patient below the rib cage and a strap having a pressure applying zone disposed over the fractured clavicle between its proximal end and the fractured portion. The strap depends diagonally downward therefrom for connection front and rear to the belt on the opposite side of the patient. Buckles are provided in the strap for adjusting the downward pressure applied to the clavicle. A sling engages the elbow of the patient for applying upward pressure to the distal end of the clavicle via the humerus and the acromion. A pressure pad having a strip of radio-opaque material is sewn into a pressure pad which is disposed against the body in the zone of pressure application in order to aid in the orthopaedic procedure.

23 Claims, 4 Drawing Figures

ORTHOPAEDIC APPLIANCE FOR USE IN TREATING FRACTURED CLAVICLES

FIELD OF THE INVENTION

The present invention relates to medical devices, and more particularly, the present invention relates to a splint for use in a non-surgical orthopaedic procedure for treating fractured clavicles.

BACKGROUND OF THE INVENTION

Most fractures of the clavicle occur in the middle region between the proximal end which is connected to the sternum and the distal end which is connected to the acromion via the acromioclavicular joint. While some clavicle fractures may be treated surgically, in most instances, it is preferable for fractured clavicles to be treated in a non-surgical manner, either because of the age or condition of the patient or because of cosmetic considerations. For instances, surgical treatment of fractured clavicles carries with it possible complications resulting from migration of intramedullary pins, broken pins, and healing of the incision itself. Moreover, about 5% of the fractured clavicles which are treated surgically result in a non-union of the fracture. Furthermore, surgical treatment is expensive due to the cost of the surgery and the subsequent hospitalization.

BRIEF DESCRIPTION OF THE PRIOR ART

For the past 20-25 years, many fractured clavicles have been treated in a non-surgical manner using so-called figure-of-eight splints, such as the McLeod padded clavicle splint disclosed in U.S. Pat. No. 3,338,236. The McLeod figure-of-eight splint comprises a pair of tubular knit pads sewn to straps and diverging in a V-shaped configuration from a common connecting pad adapted to be placed against a patient's back several inches below the base of the neck. When applied, the straps extend from the connecting pad over both clavicles and under both axillae or armpits, and return to the pad where they are adjustably fastened, as by buckles.

It is important for a fractured clavicle to be properly aligned and maintained in proper alignment during the healing process. This is because a fractured clavicle can heal even if adjacent portions are not in exact alignment. If healed when improperly aligned, fractured clavicles can develop callus, i.e. a bulbous bone mass, adjacent to the fracture, and the callus appears as an unattractive lump under the skin.

While these conventional figure-of-eight splints may function satisfactorily if applied properly to a patient under the right conditions, such splints have certain limitations. For instance, as a result of a careful study of conventional figure-of-eight splints with regard to the pathobiomechanical aspects of the fractures for which their use is indicated, it has been determined that they may not always apply to the fractured clavicle forces which insure proper alignment of the fractured portions of the clavicle. This is because when a clavicle is fractured, the distal end thereof is pulled downwardly by the weight of the arm connected thereto via the acromioclavicular joint. At the same time, the opposite fractured portion of the clavicle is being pulled upwardly by the clavicular portion of the sternocleidomastoid muscle. While the figure-of-eight splint is supposed to lift the distal end of the clavicle, it is believed that in actual practice the figure-of-eight splint applies downward pressure on the distal end of the clavicle in the direction opposite the direction desired for proper alignment of the fractured clavicle. As a result, in some situations, the figure-of-eight splint may actually hinder proper healing.

Conventional figure-of-eight splints used to treat fractured clavicles have other disadvantages. For instance, they necessarily limit mobility of both arms of the patient, thereby inconveniencing the patient in his daily routine. Since portions of the figure-of-eight splint pass under the axillae, they can interfere with circulation in the arms if applied too tightly. Furthermore, figure-of-eight splints tend to absorb perspiration, thereby causing hygienic problems.

Acromioclavicular braces are available for use in the treatment of dislocated separated A-C joints. Such a brace sold by Howmedica comprises a strap which overlies the clavicle and extends under the axilla to connect to a shoulder strap at the anterior end thereof above the breast. An arm sling connects to the shoulder strap for applying upward pressure to the acromion for promoting the requisite healing action. While this brace may function satisfactorily for its intended purpose, it is not particularly well suited for non-surgically treating a fractured clavicle.

U.S. Pat. No. 4,188,944 discloses another type of acromioclavicular restoration brace. It includes a vertically disposed oval primary strap which holds a pressure pad over the acromioclavicular joint while simultaneously applying upward pressure to the joint via the humerus and acromion. A secondary strap encircles the upper portion of the chest to hold the pad in position above the acromioclavicular joint. The secondary strap may also be used to immobilize the patient's arm. While this patented appliance may function satisfactorily to promote healing acromioclavicular dislocations, it would not be suited for use in non-surgically treating a fractured clavicle.

In order to treat fractured clavicles and other broken bones effectively in a non-surgical manner, pressure is often applied to the affected bones. As noted heretofore, it is important for the pressure to be applied in the proper direction and in the proper amount if a satisfactory result is to be obtained. While it would be helpful both to the physician and to the patient to be able to observe the location of pressure application, heretofore there has not existed an efficient and effective mechanism to permit the observation of the location of pressure application by X-ray techniques.

OBJECTS OF THE INVENTION

With the foregoing in mind, it is a primary object of the present invention to provide a novel splint for use in the non-surgical treatment of fractured clavicles.

It is another object of the present invention to provide an improved orthopaedic appliance, or splint, which is designed to promote the healing of a fractured clavicle by applying a downward pressure to the proximal portion of the clavicle and an upward pressure to the distal portion thereof via the humerus and the acromion.

Another object of the present invention is to provide a unique splint which applies pressure in the proper directions to a fractured clavicle and which is designed to enable the amount and location of the applied pressure to be adjusted.

A further object of the present invention is to provide a new orthopaedic appliance which carries radio-opaque markers for assisting the physician and patient in the non-surgical orthopaedic treatment of displaced bones.

As another object, the present invention provides a novel pad having radio-opaque markers which facilitate patient cooperation and understanding when the pad is used in certain orthopaedic procedures.

A still further object of the present invention is to provide a splint which is specifically designed to treat fractured clavicles without the need for surgery and which, therefore, eliminate the possibilities of complications arising from surgery, such as infection, non-union, pin migration, broken pins, and scarring.

Yet a further object of the present invention is to provide for use on fractured clavicles, a clavicle splint which eliminates external body deformities by minimizing the formation of callus due to improper fracture alignment and by eliminating incisional scars.

Yet another object of the present invention is to provide for use in treating fractured clavicles, an orthopaedic appliance which is comfortable to wear, which can be adjusted readily, and which promotes healing of the affected fracture without unduly restricting normal activities of the patient.

Another object of the present invention is to provide an improved method of non-surgically treating a fractured clavicle.

SUMMARY OF THE INVENTION

More specifically, the present invention provides an improved orthopaedic appliance for use in non-surgically treating fractured clavicles. The orthopaedic appliance, or splint, promotes healing of the fracture by applying downward pressure to the proximal portion of the clavicle while simultaneously applying upward pressure to the distal portion thereof. To this end, the splint comprises a strap having a pressure applying zone adapted to overlie the clavicle intermediate its proximal end and the location of the fracture. The strap has anterior and posterior portions which depend diagonally downward and terminate adjacent a wide belt which encircles the patient below the rib cage. Means is provided for adjusting the point of attachment of the strap to the belt and for adjusting the length of the strap in order to vary the amount of pressure applied to the clavicle. A sling receives the patient's elbow and functions to apply upward pressure to the distal end of the clavicle via the acromion and the humerus. Preferably, radio-opaque marker material, such as a barium sulfate strip, is carried by the strap in the zone of pressure application in order to aid in the X-ray visualization of the application of pressure during the treatment. By using the orthopaedic appliance in the aforementioned method, a fractured clavicle may be treated without surgery in an efficient manner with a minimum of patient discomfort and inconvenience and without causing noticeable external disfigurement.

BRIEF DESCRIPTION OF THE DRAWINGS

The foregoing and other objects, features and advantages of the present invention should become apparent from the following description when taken in conjunction with the accompanying drawings, in which.

DESCRIPTION OF THE PREFERRED EMBODIMENT

Figure 1:
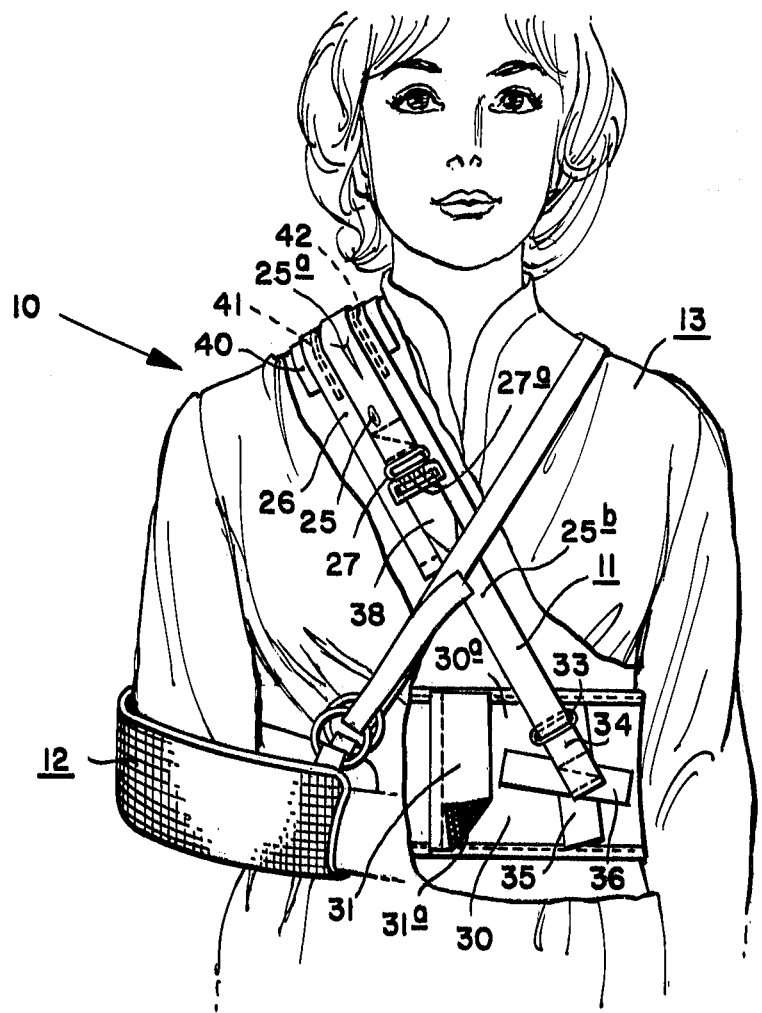
FIG. 1 is a anterior elevational view of a splint which embodies the present invention, the splint being illustrated in use treating the fractured clavicle of a female patient.

Referring now to the drawings, FIG. 1 illustrates an orthopaedic appliance, or splint, 10 which embodies the present invention. The splint 10 has two parts: a body brace 11 and an arm sling 12. The splint 10 is shown on a female patient 13 for non-surgically treating her fractured right clavicle. The body brace 11 is preferably applied under the patient's clothing, as shown, while the arm sling 12 is applied over the patient's clothing, as shown, or underneath clothing to prevent external rotation of arm.

Before proceeding with a discussion of the structure and function of the splint 10, a brief review of certain anatomical terms and their interrelationships may be in order.

Figure 3:
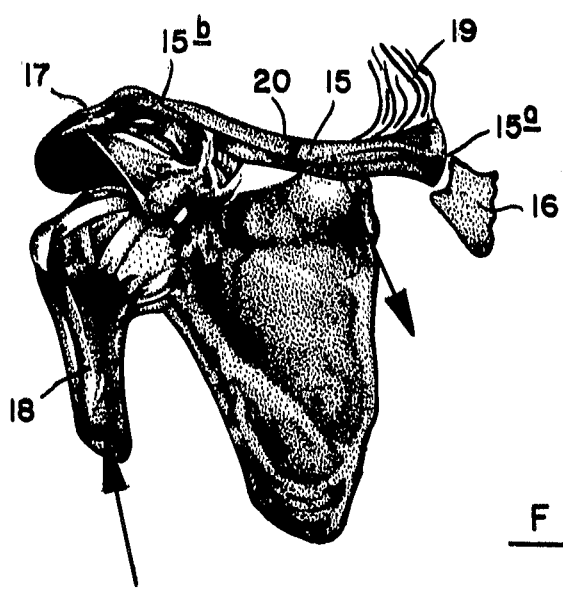
FIG. 3 is an anterior view of the interrelationship of some of the various bones and ligaments in the shoulder of the patient illustrated in FIG. 1.

Referring now to FIG. 3, it may be seen that the clavicle 15 is the slightly curved bone which extends in a generally horizontal direction between the sternum 16 and the acromion 17. The clavicle 15 has a proximal end 15a which is joined to the sternum 16 and a distal end 15b which connects to the acromion 17 by means of the acromioclavicular joint. The acromion 17 overlies the upper end of the humerus 18, the lower end of which is connected to what is commonly called the elbow joint. The clavicular portion of the sternocleidomastoid muscle 19 extends upwardly from the proximal portion 15a of the clavicle 15 in the neck. For purposes of illustration, the clavicle has been illustrated with its proximal and distal portions in its normal position with a fracture 20 illustrated in about the middle of the clavicle 15 where about 80% of all fractures occur. While various muscles and ligaments are present in the shoulder, they have been omitted from the illustration for purposes of clarity.

In a typical fracture of the clavicle 15, the clavicular portion of the sternocleidomastoid muscle 19 tends to pull the proximal portion 15a of the clavicle upward from the sternoclavicular joint. At the same time, the distal end 15b of the clavicle 15 tends to drop due to the force of gravity acting downwardly on the humerus 18 via the acromion 17. While the figure-of-eight splints discussed heretofore have been utilized to treat fractures of the clavicle 15, they have not been particularly well suited for use in treating patients having fractured clavicles in a manner which maximizes patient comfort and which minimizes patient inconvenience.

Figure 2:
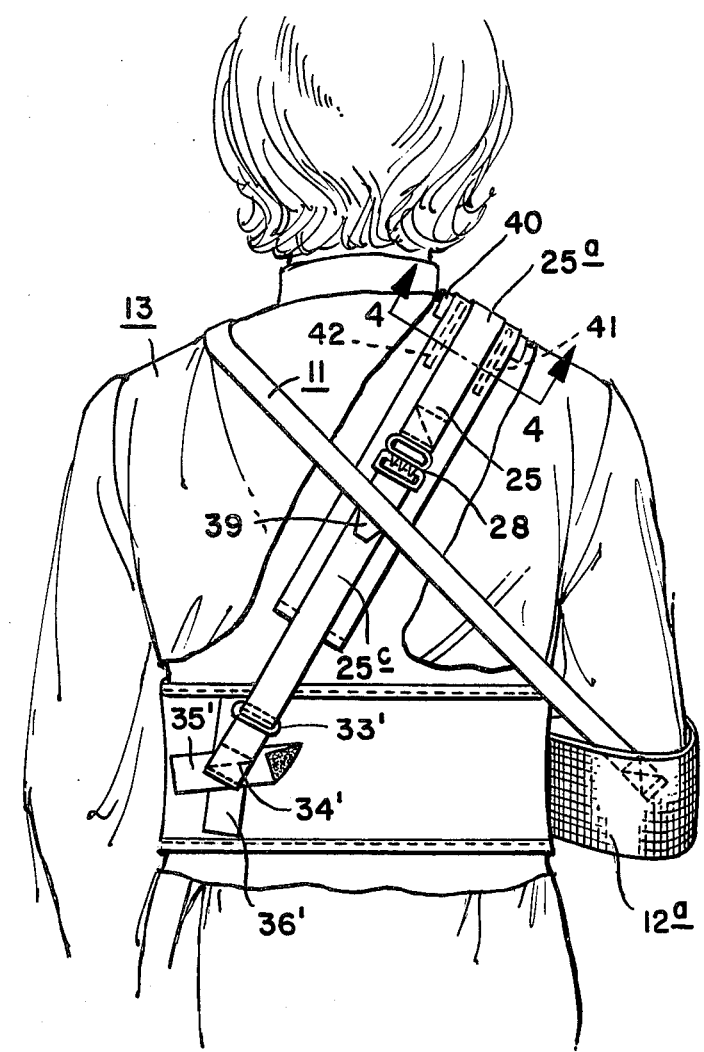
FIG. 2 is a posterior view of the splint illustrated in FIG. 1.

The splint 10 of the present invention overcomes the limitations of conventional figure-of-eight splints noted heretofore. To this end, downward pressure is applied to the clavicle 15 between its proximal end 15a and the location of the fracture 20 while upward pressure is applied to the distal end 15b via the humerus and acromioclavicular joint. As best seen in FIG. 1, the brace portion 11 of the splint 10 of the present invention comprises a strap 25 having a pressure applying portion 25a adapted to overlie the clavicle 15 between the location of the fracture 20 and the proximal end 15a thereof. The strap 25 has an anterior portion 25a which depends diagonally downward from the pressure applying portion 25a across the chest of the patient to terminate at a location below the rib cage and vertically below the opposite unbroken clavicle. As best seen in FIG. 2, the strap 25 also has a posterior portion 25c which depends diagonally downward from the pressure applying portion 25a and terminates below the rib cage and vertically below the opposite unbroken clavicle behind the point of termination of the anterior strap portion 25b. An elongated pressure pad 26 of tubular knit, cotton or other cloth material is sewn to the inside of the strap 25 in the pressure applying zone 25a thereof. If desired, a conventional resilient, adhesive-backed foam rubber pressure pad may be applied directly to the patient underneath the pad 26 to apply pressure to the affected area as discussed hereinafter.

In order to apply pressure in the downward direction to the proximal portion of the clavicle 15 indicated by the arrow in FIG. 3, and thereby to counteract the upward pull on the clavicle 15 by the clavicular portion of the sternocleidomastoid muscle 19, the brace 11 includes a belt 30 which encircles the patient's abdomen below the rib cage transverse to the patient's spinal column. As best seen in FIG. 1, the belt 30 is relatively wide (about six inches) and has an outer fabric surface 30a which is designed to cooperate with the plurality of minute hooks of a Velcro-type fastener. Preferably, a strip of Velcro-type fastener hooks indicated at 31a in FIG. 1 is connected across one end of the belt 30 and is adapted to interengage the material of the outer surface to maintain the belt in any adjusted position. Because the function of this type of fastener is well known, further description is not believed necessary at this juncture. Suffice it to say that the belt 30 may be placed around the patient's waist and tightened simply by placing the strip 31 of the hooks over the appropriate location on the outer surface 30a of the belt 30 and pressing the strip 31 firmly against the surface 30a to interengage the hooks 31a with the fabric surface 30a. Because the belt 30 is relatively wide and engages the patient below the rib cage, it tends to resist upward movement caused by normal activities of the patient, even when subjected to upward pulling forces applied in the manner to be described.

The belt 30 cooperates with the strap 25 to apply the requisite downward pressure to the proximal portion of the clavicle 15. For this purpose, the lower ends of the anterior and posterior portions 25b and 25c of the strap 25 are releasably fastened to the belt 30 in a manner which affords both lengthwise adjustment of the strap 25 and adjustment of its point of connection to the belt 30. In the illustrated embodiment, the anterior connection is provided by a metal loop 33 carried by a short length of strap 34 which is sewn onto a pair of Velcro-type hook strips 35 and 36 disposed in a generally cruciform arrangement. By virtue of the Velcro-type strips, the assembly 35-36 may be adjusted both vertically and horizontally on the belt 30 simply by disengaging the strips 35 and 36 from the belt 30 and replacing them at a different location. This also has the advantage of enabling the angle of disposition of the strap 25 to be adjusted in order to enable the splint 10 to accommodate patients of various ages and stature. The posterior portion 25c of the strap 25 is similarly connected to the belt 30 at the rear by means of a like assembly of connecting elements 33'-36'. Thus, both front and rear adjustable strap mountings are provided. If desired, portions of the strap 25 may be provided with elastic to assist in maintaining the desired degree of downward pressure.

In order to afford adjustment of the amount of pressure applied downwardly to the clavicle 15, a pair of buckles 27 and 28 are connected to the strap at opposite ends of its pressure applying zone 25a. Each buckle, such as the buckle 27, has a series of teeth 27a which are adapted to engage the strap inwardly of its free end 38 after the same have been passed through the loop 33 and returned upwardly alongside the depending portion which lays against the patient's body. The posterior portion 25c of the strap 25 is similarly disposed and has a free end 39. Thus, by pulling on the free ends 38 and 39 relative to the buckles 27 and 28, the physician can adjust the tension in the strap 25 in order to obtain the desired amount of pressure to be applied to the clavicle. The teeth of the buckles 27 and 28 function in a well known manner to prevent the tension from inadvertently being relieved while affording ready adjustability of tension should such be indicated at any point in the process of treatment. If desired, a strip of Velcro-type hooks may be used to provide the desired releasable fastening in lieu of the buckles indicated.

Generally, it is also desirable to adjust the point of application and/or the amount of pressure applied by the pressure-applying strap portion 25a. This can be readily achieved by inserting one or more pads of various thickness, such as the pad 40 illustrated underneath the pad 26 carried by the strap 25. The number of pads 40 to be utilized is best determined by the treating physician. The pads so used may be of resilient natural or synthetic materials, such as foam rubber pads which can be temporarily secured to the desired region by a suitable adhesive as well known in the art.

For the purpose of applying upward pressure to the distal end 15b of the clavicle 15, the splint 10 includes the sling 12. The sling 12 comprises a fabric pocket 12a which receives the patient's elbow and forearm in the customary manner. The sling 12 also includes a strap 12b which extends diagonally upward across the clavicle opposite the fractured clavicle and downwardly to connect to the pocket 12a at the rear thereof. See FIG. 2. The sling 12 thus functions in a well known manner to apply force upwardly in the direction indicated by the arrow in FIG. 3 to the distal end 15b of the clavicle 15 via the humerus and the acromioclavicular joint.

Figure 4:
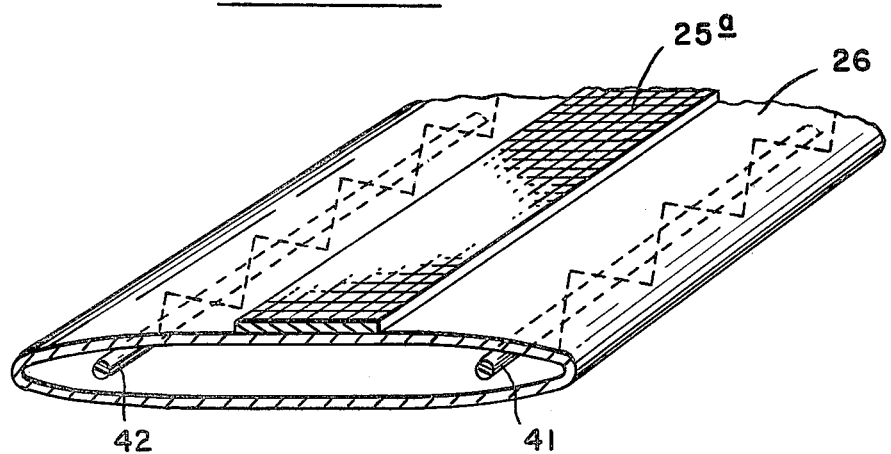
FIG. 4 is an enlarged, fragmentary perspective sectional view taken on line 4—4 of FIG. 2 of a pressure pad which is fabricated in accordance with the present invention.

In order to assist the physician in utilizing the splint 10 to treat the patient 13 in the manner described heretofore, it has been found highly beneficial for the physician to be able to observe the locations of pressure application in X-rays. Not only does this assist the physician, but it also helps the physician to explain to the patient the location of pressure application and the need for using the splint in a particular manner, thereby improving patient understanding of the procedure and cooperation therewith. To this end, marker means is incorporated into the body of the pad 26 which is carried by the strap 25. In the present instance, the marker means includes at least one elongated strip of radio-opaque marker material, such as a barium sulfate strip 41 of the type used in general surgical sponges, carried in the pressure applying zone 25a of the strap 25. The barium sulfate strip 41 is contained completely within the pad 26 and extends over the clavicle 15 of the patient 13 in the manner illustrated in FIGS. 1 and 2. If desired, a companion strip 42 may also be contained within the pad 26 to bracket the zone of pressure application. Preferably, the pad 26 is fabricated of a tubular cotton-polyester knit stockinette, and the barium sulfate strips 41 and 42 are sewn into the stockinette 26 before it is applied to the strap 25 in the manner illustrated. See FIG. 4.

After the splint 10 has been applied to the patient in the manner illustrated in FIGS. 1 and 2, and an X-ray examination is made of the fractured clavicle, the barium sulfate strips 41 and 42 will appear on the X-ray films as lines disposed transverse to the clavicle. This enables the physician to see exactly the location of pressure application and helps the physician explain to the patient the biomechanics involved in the use of the splint 10 in promoting the healing of the fractured clavicle.

While the barium sulfate strips have been illustrated in combination with a pad 26 included in the splint 10 for healing a fractured clavicle, it should be apparent that there are many other applications involving the non-surgical treatment of dislocations and fractures where a pad having such strips may find substantial utility. Radio-opaque markers formed of barium sulfate strips are preferred because they are flexible and, are, therefore, able to be wrapped around the affected area undergoing treatment. Strips of barium sulfate sold under the RAY-TEC trade designation and having a diameter of about 2 mm. have been tested and found to provide an adequate image on an X-ray print of the area around which the pad containing the strip has been wrapped.

The splint 10 of the present invention has been used successfully to treat patients having broken clavicles in a non-surgical manner. By way of example, a 57 year old male who sustained a severely comminuted fracture of the mid-shaft portion of the right clavicle was treated with the splint 10 of the present invention. The splint 10 was applied in the manner described heretofore, i.e. with pressure being applied downwardly between the fracture and the proximal end of the clavicle and with pressure being applied in the opposite direction upwardly to the distal end of the clavicle via the humerus. The period of treatment lasted about ten weeks. X-rays taken of the affected area revealed that the fracture was almost completely healed using the splint 10 in the manner described for the aforementioned time period.

In view of the foregoing, it should be apparent that the present invention now provides both an improved splint and method of employing it to treat a patient having a fractured clavicle. The use of radio-opaque barium sulfate markers in a pad which can be wrapped around an area of broken or displaced bones and joints has been found to be beneficial in aiding the non-surgical treatment thereof by improving better physician and patient understanding of the biomechanics involved in the treatment procedure.

Thus, while a preferred embodiment of the present invention, along with its method of application, has been described in detail, various modifications, alterations and changes may be made without departing from the spirit and scope of the present invention as defined in the appended claims.

I claim:

1. For use in treating a patient having a clavicle fractured between its proximal end which is joined to the sternum and its distal end which is joined to the acromion overlying the humerus, a splint comprising:
    a belt adapted to encircle the patient's abdomen below the rib cage transverse to the spinal column;
    a strap having a pressure applying zone adapted to overlie the clavicle between its proximal end and the location of the fracture, said strap having an anterior portion depending diagonally downward from said pressure applying zone and across the patient's rib cage to a location adjacent said belt and to the side opposite the fractured clavicle, said strap also having a posterior portion depending diagonally downward from said pressure applying zone and across the patient's back to a location adjacent said belt on the side opposite the fractured clavicle;
    means connecting said front and rear strap portions to said belt;
    means for tensioning said strap to cause it to apply downward pressure to said clavicle between its proximal end and the fracture; and
    sling means adapted to engage the patient's elbow and forearm and engaging over the patient's opposite clavicle for applying pressure upwardly via the humerus and acromion to the distal end of the clavicle;
    whereby pressure is applied in opposite directions to the fractured clavicle for urging it into proper juxtaposition for promoting healing.

2. The splint according to claim 1 wherein said tensioning means includes buckles in said anterior and posterior portions of said strap affording length adjustment thereof.

3. The splint according to claim 1 wherein said tensioning means includes at least one pad interposed between said pressure applying zone of said strap and said clavicle.

4. The splint according to claim 1 including means affording adjustment of the location of said strap connecting means to said belt.

5. The splint according to claim 1 including means affording both horizontal and vertical adjustment of said strap connecting means to said belt.

6. The splint according to claim 5 wherein said horizontal and vertical adjustment affording means includes a loop adapted to receive said strap, a pad connected to said loop and having a plurality of small closely spaced hooks, and means providing a fabric surface on said belt for releasably engaging said hooks.

7. The splint according to claim 1 wherein said tensioning means includes at least one buckle in said strap affording lengthwise adjustment thereof and at least one pad interposed between said pressure applying zone and said fractured clavicle.

8. The splint according to claim 1 wherein said belt has a width of about 6 inches and has a strip of small closely-spaced hook affording releasable overlapping connection of the ends of the belt.

9. The splint according to claim 1 including a flexible radio-opaque marker carried by said strap in said pressure applying zone.

10. The splint according to claim 9 wherein said marker includes a strip of barium sulfate disposed lengthwise of said strap in said pressure applying zone.

11. The splint according to claim 10 including an elongated pad connected to the inside of said strap and extending in opposite directions from said pressure applying zone, and wherein said barium sulfate strip is carried by said pad.

12. The splint according to claim 11 wherein said pad is of tubular cloth construction and said barium sulfate strip is sewn into said pad.

13. The splint according to claim 1 wherein said sling means includes a fabric pocket adapted to receive the patient's elbow and a retention strap adapted to extend over the patient's other clavicle for applying said upward pressure.

14. The splint according to claim 1 including means on said strap and on said belt affording lengthwise adjustment of said strap and angular adjustment thereof relative to said belt.

15. For use in an orthopaedic procedure to treat a patient having displaced bone portions, a splint comprising a flexible pad adapted to be placed adjacent to the displaced bone portions, a length of flexible radio-opaque marker material carried in said pad, and means for causing said pad to apply pressure to the displaced bone portions for urging the same into normal juxtaposition, whereby the radio-opaque material becomes visible in X-ray films of the displaced bone portions for aiding in the performance of the orthopaedic procedure.

16. The spling according to claim 15 wherein said radio-opaque material includes at least one strip of barium sulfate carried within said pad.

17. The splint according to claim 16 wherein said pad is of tubular cloth construction and said barium sulfate strip is sewn into said pad.

18. The splint according to claim 15 wherein said pad containing said marker material is elongated and is adapted to be disposed diagonally across the clavicle of a human body, and said pressure applying means cooperates with said pad to maintain said diagonal disposition during said orthopaedic procedure.

19. The splint according to claim 18 wherein said pressure applying means includes a belt adapted to encircle the patient's body below the rib cage, and a diagonal strap connected front and rear to said belt for securing said pad against the patient's body.

20. The splint according to claim 19 including means in said strap between said pad and said belt for adjusting the tension in the strap and thereby varying the pressure applied by said pad.

21. A method of non-surgically treating a patient having a clavicle fractured in the medial zone between its proximal and distal ends, comprising the steps of:
   applying downward pressure to the clavicle between its proximal end and the fracture,
   simultaneously applying upward pressure to the distal end of the clavicle via the humerus and acromion, and
   maintaining said pressure application for a period of time sufficient to afford healing of the fracture.

22. The method according to claim 21 wherein said downward pressure is applied by a pressure pad carried by a strap disposed diagonally across the patient's torso, and including the step of tensioning said strap on said diagonal.

23. The method according to claim 21 wherein said upward pressure is applied by means of a sling receiving the patient's elbow and extending over the patient's other clavicle.

* * * * *